(12) United States Patent
Scheller et al.

(10) Patent No.: US 8,283,376 B2
(45) Date of Patent: Oct. 9, 2012

(54) USE OF SUBSTITUTED 2-AMINOTETRALINS FOR PREVENTIVE TREATMENT OF PARKINSON'S DISEASE

(75) Inventors: Dieter Scheller, Neuss (DE); Frank Dressen, Vettweiβ (DE)

(73) Assignee: UCB Pharma GmbH, Monheim (DE)

( * ) Notice: Subject to any disclaimer, the term of this patent is extended or adjusted under 35 U.S.C. 154(b) by 733 days.

(21) Appl. No.: 10/585,609

(22) PCT Filed: Dec. 23, 2004

(86) PCT No.: PCT/EP2004/014656
§ 371 (c)(1), (2), (4) Date: Mar. 12, 2007

(87) PCT Pub. No.: WO2005/063238
PCT Pub. Date: Jul. 14, 2005

(65) Prior Publication Data
US 2008/0146622 A1    Jun. 19, 2008

(30) Foreign Application Priority Data
Dec. 24, 2003    (DE) .................................. 103 61 258

(51) Int. Cl.
*A61K 31/381*    (2006.01)
(52) U.S. Cl. ........ 514/438; 514/357; 514/415; 514/427; 514/399; 514/471; 549/74; 549/75; 549/77; 549/492; 549/494
(58) Field of Classification Search .................. 514/438, 514/357, 415, 427, 399, 471, 521, 523; 549/74, 549/75, 77, 492, 494, 495, 329, 335, 334; 548/503, 561, 341
See application file for complete search history.

(56) References Cited

U.S. PATENT DOCUMENTS

| 4,542,135 A | 9/1985 | Kobel et al. ................... 514/250 |
| 4,564,628 A | 1/1986 | Horn ............................. 514/438 |
| 4,722,933 A | 2/1988 | Horn ............................. 514/438 |

(Continued)

FOREIGN PATENT DOCUMENTS

CA    2 532 804    2/2005

(Continued)

OTHER PUBLICATIONS

Shoulson et. al, .Archives Neurology, vol. 60, Dec. 2003, pp. 1721-1728, published $2^{nd}$ Monday of the month which would be on Dec. 13, 2003.*

(Continued)

*Primary Examiner* — Savitha Rao
(74) *Attorney, Agent, or Firm* — Harness, Dickey & Pierce, P.L.C.

(57) ABSTRACT

The invention relates to the use of substituted 2-aminotetralins of general formula (I)

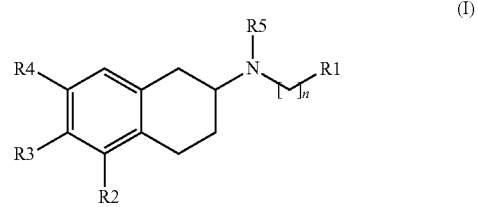

as a medicament for the preventive treatment of Parkinson's disease.

12 Claims, 1 Drawing Sheet

Neuroprotective Effect of Rotigotine

U.S. PATENT DOCUMENTS

| | | | | |
|---|---|---|---|---|
| 4,824,860 | A | 4/1989 | Owen | 514/418 |
| 4,847,253 | A | 7/1989 | Buonamici et al. | 514/253 |
| 4,885,308 | A | 12/1989 | Horn | 514/418 |
| 5,071,875 | A | 12/1991 | Horn | 514/613 |
| 5,151,446 | A | 9/1992 | Horn et al. | 514/617 |
| 5,177,112 | A | 1/1993 | Horn | 514/65 |
| 5,234,945 | A * | 8/1993 | Belluzzi | 514/438 |
| 5,382,596 | A | 1/1995 | Sleevi et al. | 514/459 |
| 5,456,745 | A | 10/1995 | Roreger et al. | 106/128 |
| 5,486,611 | A | 1/1996 | Lin et al. | 546/62 |
| 5,496,843 | A | 3/1996 | Nagata et al. | 514/411 |
| 5,545,755 | A | 8/1996 | Lin et al. | 564/428 |
| 5,614,518 | A | 3/1997 | Leeson et al. | 514/234.5 |
| 5,633,376 | A | 5/1997 | Thurkauf et al. | 544/360 |
| 5,681,956 | A | 10/1997 | Thurkauf et al. | 544/295 |
| 5,807,570 | A | 9/1998 | Chen et al. | 424/449 |
| 5,807,855 | A | 9/1998 | Bogeso et al. | 514/449 |
| 5,891,461 | A | 4/1999 | Jona et al. | 424/449 |
| 6,001,861 | A | 12/1999 | Oertel et al. | 514/367 |
| 6,010,877 | A | 1/2000 | Sathe et al. | 435/69.1 |
| 6,107,318 | A | 8/2000 | Pocchiari et al. | 514/367 |
| 6,221,627 | B1 | 4/2001 | Sathe et al. | 435/69.1 |
| 6,227,875 | B1 | 5/2001 | Wu et al. | 514/367 |
| 6,331,636 | B1 | 12/2001 | Romero et al. | 548/235 |
| 6,372,920 | B1 | 4/2002 | Minaskanian et al. | 549/75 |
| 6,884,434 | B1 | 4/2005 | Muller et al. | 424/487 |
| 7,309,497 | B2 | 12/2007 | Rimpler et al. | 424/422 |
| 7,413,747 | B2 | 8/2008 | Mueller et al. | 424/448 |
| 7,632,852 | B2 | 12/2009 | Barth et al. | 514/438 |
| 7,632,859 | B2 | 12/2009 | Li et al. | 514/438 |
| 2003/0026830 | A1 | 2/2003 | Lauterback et al. | 424/449 |
| 2003/0027793 | A1 | 2/2003 | Lauterback et al. | 514/63 |
| 2003/0166709 | A1 | 9/2003 | Rimpler et al. | 514/447 |
| 2004/0034083 | A1 | 2/2004 | Stephenson et al. | 514/406 |
| 2004/0048779 | A1 | 3/2004 | Schollmayer | 514/2 |
| 2004/0081683 | A1 | 4/2004 | Schacht et al. | 424/449 |
| 2004/0116537 | A1 | 6/2004 | Li et al. | 514/663 |
| 2004/0137045 | A1 | 7/2004 | Breitenbach et al. | 424/449 |
| 2004/0198753 | A1 * | 10/2004 | Kase et al. | 514/263.2 |
| 2004/0209861 | A1 | 10/2004 | Benavides et al. | 514/210.41 |
| 2005/0032843 | A1 | 2/2005 | Pieper et al. | 514/338 |
| 2005/0033065 | A1 | 2/2005 | Mueller et al. | 549/74 |
| 2005/0079206 | A1 | 4/2005 | Schacht et al. | 424/449 |
| 2005/0175678 | A1 | 8/2005 | Breitenbach | 424/448 |
| 2005/0182090 | A1 | 8/2005 | Mierau et al. | 514/304 |
| 2005/0197385 | A1 | 9/2005 | Scheller et al. | 514/438 |
| 2005/0260254 | A1 | 11/2005 | Breitenbach et al. | 424/449 |
| 2006/0263419 | A1 | 11/2006 | Wolff | 424/448 |
| 2007/0072917 | A1 | 3/2007 | Scheller et al. | 514/357 |
| 2007/0093546 | A1 | 4/2007 | Scheller et al. | 514/447 |
| 2007/0191308 | A1 | 8/2007 | Kramer | 514/60 |
| 2007/0191470 | A1 | 8/2007 | Scheller | 514/438 |
| 2007/0197480 | A1 | 8/2007 | Scheller et al. | 514/114 |
| 2008/0008748 | A1 | 1/2008 | Beyreuther et al. | 424/449 |
| 2008/0138389 | A1 | 6/2008 | Muller et al. | 424/448 |
| 2008/0146622 | A1 | 6/2008 | Scheller | 514/357 |
| 2008/0274061 | A1 | 11/2008 | Schollmayer et al. | 424/45 |
| 2009/0143460 | A1 | 6/2009 | Wolff et al. | 514/438 |
| 2010/0311806 | A1 | 12/2010 | Wolff et al. | 514/438 |

FOREIGN PATENT DOCUMENTS

| | | |
|---|---|---|
| CA | 2 532 859 | 2/2005 |
| CA | 2 547 820 | 6/2005 |
| CA | 2 546 797 | 7/2005 |
| CA | 2 568 850 | 2/2006 |
| EP | 1256339 | 11/2002 |
| WO | WO 93/00313 | 1/1993 |
| WO | WO 94/26703 | 11/1994 |
| WO | WO 96/31210 | 10/1996 |
| WO | WO 97/29735 | 8/1997 |
| WO | WO 99/49852 | 10/1999 |
| WO | WO 00/03715 | 1/2000 |
| WO | WO 00/02053 | 6/2000 |
| WO | WO 00/35954 | 6/2000 |
| WO | WO 00/38669 | 7/2000 |
| WO | WO 01/38321 | 5/2001 |
| WO | WO 01/39756 | 6/2001 |
| WO | WO 01/62249 | 8/2001 |
| WO | WO 02/15903 | 2/2002 |
| WO | WO 02/31499 | 4/2002 |
| WO | WO 02/38646 | 5/2002 |
| WO | WO 02/18382 | 7/2002 |
| WO | WO 02/089777 | 11/2002 |
| WO | WO 02/089778 | 11/2002 |
| WO | WO 03/007803 | 1/2003 |
| WO | WO 03/012137 | 2/2003 |
| WO | WO 03/029233 | 4/2003 |
| WO | WO 03/069332 | 8/2003 |
| WO | WO 03/076658 | 9/2003 |
| WO | WO 03/088958 | 10/2003 |
| WO | WO 2004/012719 | 2/2004 |
| WO | WO 2004/012721 | 2/2004 |
| WO | WO 2004/012730 | 2/2004 |
| WO | WO 2004/050083 | 6/2004 |
| WO | WO 2004/058247 | 7/2004 |
| WO | WO 2005/070428 | 8/2005 |
| WO | WO 2006/050976 | 3/2006 |
| WO | WO 2006/039532 | 4/2006 |

OTHER PUBLICATIONS

Abbas (1999) Hum. Mol. Genet 8, 567.
Barzilai (2001) Cell Mol. Neurobiol. 21(3), 215-235.
Becker (2002) J. Neurol. 249(Suppl. 3)III/40-III/48.
Blanchet et al. (2004) Parkinsonism and Related Disorders 10, 297-304.
Borsini (1988) Eur. J. Pharmacol. 148, 301-307.
Burn (2000) The Pharmaceutical Journal 264, 476-479.
Camicioli (2002) R. Drugs Today (Barc) 38*10, 677-686.
Carp et al. (1982) Brain Research 242, 247-254.
Chan et al. (2004) Hospital Pharmacist 11, 18-22.
Chase et al. (1995) Clinical Neuropharmacology 18(1), S207-S215.
Dawson (2002) Nature Neuroscience Supplement, vol. 5, 1058-1061.
Den Daas (1990) Naunyn-Schmiedeberg's 342, 655-659.
Domino et al. (1983) J. Pharmacol. & Experimental Therapy vol. 264(1), 221-225.
Eberhardt (2003) Toxicology Letter 139(2), 135-151.
Fahn et al. (1987) Recent Developments in Parkinson's Disease vol. II, 153-163, 293-304.
Foley et al. (2004) J. Neural Transmission 111, 1375-1446.
Gerlach (2003) Neurotox. Res. 5(1), 43-51.
Gerlach et al. (2003) J. Neural Transm. 65(Suppl.), 167-183.
Guttman (2003) Canadian Med. Assoc. Journal 168(3), 293-301.
Hackling (2002) ChemBioChem 3, 947-961.
Hagan et al. (1997) TIPS vol. 18, 156-163.
Hauser et al. (2004) Neurol. Clin. 22, S149-S166.
Henderson (2003) J. Neurol. Neurosurg. Psychiatry 74, 956.
Hobson (2003) Can. J. Neurol. Sci. 30(Suppl 1) S2-S9.
Holcomb et al. (1982) Eur. J. Pharmacol. 82, 173-178.
Hornykiewicz (2002) Encyclopedia of Life Sciences vol. 13, 695-704.
Hughes (1992) J. Neurol. Neurosurg. Psychiatry 55, 181-184.
Hutchinson et al. (1999) J. Neurol. Neurosurg. Psychiatry 67, 815-818.
Joyce (2001) Pharmacol. & Ther. 90, 231-259.
Kitada (1998) Nature 392, 605-608.
Korczyn et al. (2002) Drugs 62(5), 775-786.
Krygowska-Wajs (2000) Funct. Neurol. 15, 41.
Lee et al. (1982) Psychiatry Research 7, 111-119.
Lev (2003) Prog. Neuropsychopharm. Biol. Psychiatry 27(2), 245.
Levien (2005) Advances in Pharmacy 3(1), 62-92.
Li et al. (2000) Proceed Intl. Symp. Control Rel. Bioact. Mater, pp. 952-953.
Li et al. (2001) Pharm. Research vol. 18(11), 1509-1513.
Linazasoro (2004) Movement Disorders 19(7), 743-754.
Lucking (2000) N. Engl. J. Med. 342, 1560-1567.
Mackonochie (2003) Mar. 31-Apr. 3 Stuttgart, GER, Drug Discovery Tech. 2003 Seventh Annual Conference and Exhibition, vol. 6, 420-422.
Matsumine (1997) Am. J. Hum. Genet. 60, 588.
Metman (2001) Clinical Neuropharmacology 24(3), 163-169.

Michel et al. (2002) Rev. Neurol. (Paris) 158 Spec No. 1, pp. 7S24-7S32.
Modigh et al. (1984) Neurotransmitter & Receptor Mechanisms, 18-27.
Muramatsu et al. (2003) Glia 42, 307-313.
Newman-Tancredi et al. (2002) J Pharmacology and Experimental Therapeutics 303(2), 805-814.
Nurse et al. (1984) Neurochemical Research 9(9), 1231-1238.
Nussbaum (2003) N. Engl. J. Medicine 348(14),1356-1364.
Pankratz (2003) Am. J. Hum. Genet. 72, 1053-1057.
Park (2002) Drug Delivery Technology 2(5), July//August, http://www.drugdeliverytech.com/cgi-bin/issues.cgi?idIssue=6 and http://www.drugdeliverytech.com/cgi-bin/articles.cgi?idArticle=60.
Pascual (1992) Annals of Neurology 32(5), 703-707.
Polymeropoulos (1997) Science 276, 2045-2047.
Prunier (2003) NeuroImage 19, 810-816.
Rammsayer (1997) Int. J. Neurosci. 91, 45.
Riederer (2000) J. Neurol. 247(4), IV/36-IV/37.
Scriabine (2003) CNS Drug Reviews 9(4), 389-395.
Sharma (2002) Neurol. Clin. N. Am. 20, 759-778.
Stern (2004) Annals of Neurology 56(2), 169-170.
Stiasny-Kolster et al. (2000) Sleep, May 1, 23(3), 1-6.
Stichel and Scheller (2005) EFNS Conference, "Rotigotine Prevents Neurodegeneration in a Mouse Model of Parkinson's Disease".
Stockmeier et al. (1997) Neuropsychopharmacology 16(2), 162-173.
Swart (1993) Toxicology Methods 3, 279, 289 last paragraph.
Swart (1994) J. Analytical Toxicology 18, 71-77.
Swart (1995) Pharmaceutical Sciences 1, 437-440.
Tassin (1998) Am. J. Hum. Genet. 63, 88-94.
Tuite (2003) Expert Opin. Investig. Drugs 12(8), 1335-1352.
Valente (2001) Am. J. Hum. Genet. 68, 895.
van der Geest et al. (1997) Pharm. Research vol. 14, 1798-1803.
Van Dujin (2001) Am. J. Hum. Genet. 69, 629-634.
Vanacore (2002) Neurol. Sci. 23, S119.
Vila (2003) Nat. Rev. Neurosci 4(5), 365.
Waters (2005) Movement Disorder 20(1), S38-S44.
Wenning et al. (2004) Lancet Neurology 3, 93-103.
Balsara et al. (1982) Ind. J. Physiol. Pharmac. 26(3):183-195.
Collado-Seidel et al. (1999) CNS Drugs 12(1):9-20.
Den Daas (1990) Naunyn-Schmiedeberg's Archives of Pharmacology 341, 186-191.
EMEA (2005) Scientific discusiOm (Siol), www.emea.wropa.eulhumandoCSmDFslEPAFVsif I/0591 97ei16.M~ 9 pp.
Hirsch (2003) Ann NY Academy Science 991, 214-228.
Hoehn (1992) *Parkinson's Disease* 10(2):331-339.
Jackson et al. (1989) NaunynSchmiedeberg's *Arch*. Pharmacol. 340:35S365.
Johnston & Brotchie (2004) Curr. Opin. Invest. Drugs 5(7):720-726.
Kulkarni & Verma (1992) Drugs of Today 28(3):201-217.
Mouradian & Chase (1989) Curr. Opin. Neurol. Neurosurg. 2:30+313.
Mucke (2003) IDrugs 6(9), 894-899.
Neophytides et al. (1982) J. Neurology Neurosurgery Psychiatry 45, 261-263.
Parkinson Study Group (2003) Arch. Neurol. 60(12), 1721-1728.
Paulus & Trenkwalder (2006) Lancet Neurol. 5 (neurolosv.thelancet.com), 9 pp.
Pierot (1988) J. Neurological Sciences 86, 291-306.
Sherman (2001) "Augmentation strategy aids treatment-resistant depression. (Dopamine Agonist).(pramipexole for mental depression)." Clinical Psychiatry News p. 1-2.
Strange (1993) Neurochem. Int. 22(3):223-236.
Timmerman (1993) Pharm. World Sci. 15(2):90-92.
Wikstrom (1992) in Ellis & Luscombe, eds. "Progress in Medical Chemistry" vol. 29, pp. 199-216; Elsevier.

Office Action, dated Dec. 10, 2008 issued in U.S. Appl. No. 11/060,997.
Office Action, dated Jun. 29, 2009 issued in U.S. Appl. No. 11/060,997.
Office Action, dated Mar. 29, 2010 issued in U.S. Appl. No. 11/060,997.
Office Action, dated Aug. 5, 2009 issued in U.S. Appl. No. 10/593,964.
Office Action, dated Sep. 12, 2008 issued in U.S. Appl. No. 10/429,283.
Office Action, dated Mar. 30, 2009 issued in U.S. Appl. No. 10/429,283.
Office Action, dated Dec. 23, 2009 issued in U.S. Appl. No. 10/429,283.
Office Action, dated Oct. 1, 2010 issued in U.S. Appl. No. 10/429,283.
Office Action, dated Aug. 16, 2010 issued in U.S. Appl. No. 11/239,701.
Den Daas, et al. (1991) "Orally active carbamate prodrugs of the selective dopamine agonist N-0437: In-vivo activities in the 6-OHDA turning model and In-vitro activities." J. Pharm. Pharmacol. 43:11-16.
Gerlach, et al. (2003) "Neuromelanin and its interaction with iron as a potential risk factor for dopaminergic neurodegeneration underlying Parkinson's disease." Neurotoxicity Research 5(1):43-51.
Hughes, et al. (1992) "Accuracy of clinical diagnosis of idiopathic Parkinson's disease: a clinico-pathological study of 100 cases." Journal of Neurology, Neurosurgery, and Psychiatry 55:181-184.
Kihara, et al. (2002) "Protective effect of dopamine D2 agonists in cortical neurons via the phosphatidylinositol 3 kinase casade." J. Neurosci. Res. 70:274-282.
Mark (2001) "Lumping and splitting the Parkinson plus syndromes." Movement Disorders 19(3):607-627.
Martinez-Martin, et al. (1994) "Unified Parkinson's disease rating scale characteristics and structure." Movement Disorders 9(1):76-83.
McKay, et al. (2008) "Will stem cell biology generate new therapies for Parkinson's disease?" Neuron 58:659-661.
Nair, et al. (2003) "Activation of phosphoinositide 3-kinase by $D_2$ receptor prevents apoptosis in dopaminergic cell lines." Biochem. J. 373:25-32.
Oertel, et al. (2003) "New aspects in the treatment of Parkinson's disease." Akt Neurol 30(Suppl 2):S263-265.
Oertel, et al. (2003) "New aspects in the treatment of Parkinson's disease." Akt Neurol 30(Suppl 2):S263-265 (English Translation).
R & D Focus Drugs News, Aug. 20, 2001, "Drug delivery system, transdermal rotigotine Schwartz clinical data (treatment of Parkinson's disease." IMS World Pulications Ltd. ISSN:1350-1135.
Rascol, et al. (2002) "Treatment interventions for Parkinson's disease: an evidence based assessment." Lancet 359:1589-1598.
Schapira (2002) "Neuroprotection and dopamine agonists." Neurology 58(Suppl 1):S9-S18.
Scheller, et al. (2007) "Rotigotine treatment partially protects from MPTP toxicity in a progressive macaque model of Parkinson's disease." Experimental Neurology 203:415-422.
Scheller, et al. (2008) "Neuroprotective effects of rotigotine in the acute MPTP-lesioned mouse model of Parkinson's disease." Neuroscience Letters 432:30-34.
Takashima, et al. (1999) "Bromocriptine protects dopaminergic neurons from levodopa-induced toxicity by stimulating $D_2$ receptors." Exp. Neurol. 159:98-104.
Thomas, et al. (2007) "Dopa-responsive pseudo-orthostatic tremor in Parkinsonism." Movement Disorders 22(11):1652-1656.
Van der Weide, et al. (1988) "The enantiomers of the D-2 dopamine receptor agonist N-0437 discriminate between pre- and postsynaptic dopamine receptors." Eur J Pharmacol 146:319-326.

* cited by examiner

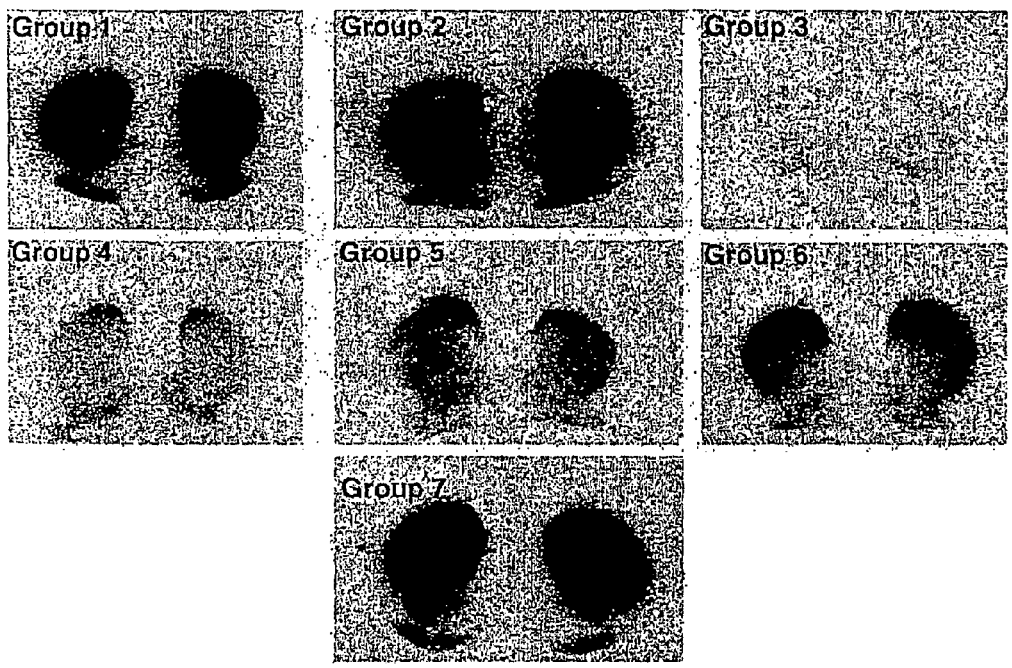
Fig. 1: Neuroprotective Effect of Rotigotine
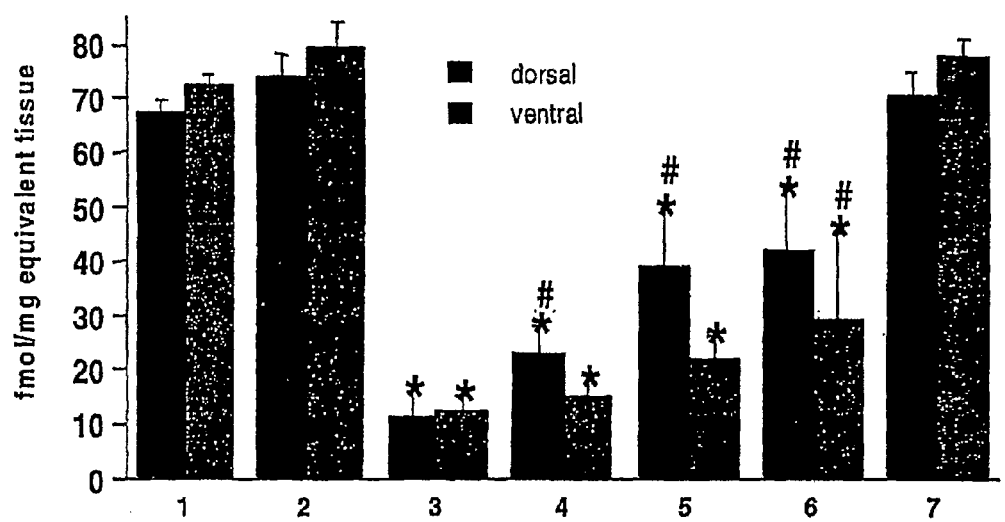
Fig. 2: Neuroprotective Effect of Rotigotine

USE OF SUBSTITUTED 2-AMINOTETRALINS FOR PREVENTIVE TREATMENT OF PARKINSON'S DISEASE

This application is a U.S. national stage filing under 35 U.S.C. §371 of International Application No. PCT/EP2004/014656 filed on Dec. 23, 2004, which claims priority of German Application No. DE 103 61 258.0 filed on Dec. 24, 2003. The disclosure of each of the applications identified in this paragraph is incorporated herein by reference in its entirety.

The subject matter of the present application is related to that of co-pending application Ser. No. 11/060,997 filed on Feb. 17, 2005.

Parkinson's disease occurs as a result of a chronic, progressive degeneration of neurones, the cause of which has not yet been completely clarified. It is clinically manifested in the form of the cardinal symptoms of resting tremors, rigidity, bradykinesia and postural instability.

Primarily used as medicaments for alleviating the motor symptoms are levodopa, dopamine agonists such as, for example, rotigotine, pramipexole, bromocriptine, ropinirole, cabergoline, pergolide, apomorphine and lisuride, anticholinergic agents, NMDA antagonists, β-blockers as well as the MAO-B inhibitor selegeline and the COMT inhibitor entacapone. Most of these active substances intervene in the dopaminergic and/or cholinergic signal cascade and symptomatically influence in this manner the motor disturbances that are typical of Parkinson's disease.

The therapy of morbus Parkinson has, to date, been initiated with the onset of the cardinal symptoms. Morbus Parkinson is generally deemed to be clinically confirmed if at least two of the four cardinal symptoms (bradykinesia, resting tremors, rigidity and postural instability) can be determined and L-dopa has an effect (Hughes (1992) *J. Neurol. Neurosurg. Psychiatry* 55:181). Unfortunately, however, patients with Parkinson's disease only develop the motor disturbances once approximately 70% to 80% of the dopaminergic neurones in the substantia nigra (SN) have been irreversibly damaged (Becker et al. (2002) *J. Neurol.* 249 (Suppl. 3:III): 40; Homykiewicz (2001), *Encyclopaedia of Life Science* 1). The chances of a therapy with lasting effects are minimal at this time. It is thus desirable to commence therapy as early as possible.

Current clinical observations as well as anatomical and genetic research now show that it is possible to both diagnose patients with Parkinson's disease at an early stage and to identify high-risk patients.

The following, for example, can thereby be used as diagnostic markers:

Biochemical markers, such as neuromelanin (Gerlach (2003) *Neurotox. Res.* 5:35; WO 02/31499), S-100 beta (Muramatsu (2003) *Glia* 42:307), alpha synuclein (WO 03/069332; WO 00/02053) or parkin protein (Sharma (2002) *Neurol. Clin. N. Am.* 20:759) and semaphorin (WO 03/007803).

Genetic markers, such as the park genes 1-8 (Guttman (2003) *CMAJ* 4:168); CYP2D6-B (WO 03/012137), chromosome 2q 36-37 (Pankratz (2003) *Am. J. Hum. Gen.* 72, e-pub), a-synuclein (Polymeropoulos (1997) *Science* 276:2045) or mutations in CYP2D6-B and GSTM1 deletion (WO 03/012137).

Imaging methods, such as ultrasound examination of the SN size, possibly in combination with other methods (Becker et al. (2002) *J. Neurol.* 249 (Suppl 3:III):40) or MRI (Hutchinson & Raff (1999) *J. Neurol. Neurosurg. Psychiatry* 67(6):815-818).

Imaging methods such as PET or SPECT (Prunier et al. (2003) *Neuroimage* 19(3):810-816).

Sensory disorders or behavioral abnormalities, such as sleep and olfactory disorders, in particular, sleep disorders of the "REM behavior disorder" type, (Henderson (2003) *J. Neurol. Neurosurg. Psychiatry* 74:956) or cognitive abnormalities (Rammsayer (1997) *Int. J. Neurosci.* 91:45).

Organic problems such as constipation (Krygowska-Wajs (2000) *Funct. Neurol.* 15:41).

Depression (Camicioli (2002) *Drugs Today (Barc.)* 38(10): 677-686).

Short-term movement anomalies, such as chorea or orthostatic abnormalities.

Combinations of the aforementioned markers (Stem (2004) *Ann. Neurol.* 56:169).

This thus creates the opportunity to influence the process of the disease at a point when more neurones are still present than is the case at the time of onset of several cardinal motor symptoms of morbus Parkinson, and to thus protect a quantitatively greater number of neurones. It can be expected that the administration of an effective neuroprotective agent at an early stage will significantly delay the disease process: The earlier a therapy can be initiated, the greater the chances of a long-lasting prevention of the onset of symptoms that lower the quality of life.

There is thus a need for medicaments that are not only able to influence dopaminergic transmission and alleviate the symptoms of morbus Parkinson in advanced stages, but that are also able to reverse, prevent or at least significantly slow down the progressive destruction of dopaminergic neurones in the early, largely motor-asymptomatic stages of Parkinson's disease (Dawson (2002) *Nature Neuroscience Supplement* 5:1058).

Substituted 2-aminotetralins are known from U.S. Pat. Nos. 4,564,628, 4,885,308, 4,722,933 and WO 01/38321. These are substances having a dopaminergic effect, which are known for the symptomatic treatment of Parkinson's disease. In clinical studies, rotigotine ((−)-5,6,7,8-tetrahydro-6-[propyl[2-(2-thienyl)ethyl]amino]-1-naphthol) in particular has proven itself to be an effective transdermally available anti-Parkinson drug. WO 02/089777 describes, for example, the transdermal administration of rotigotine to patients with Parkinson's disease and the associated improvement in the UPDRS (Unified Parkinson's Disease Rating Scale) score. The UPDRS score is an important instrument for diagnosing and monitoring the progression and/or therapy of patients with Parkinson's disease (Fahn et al. (1987) Unified Parkinson's Disease Rating Scale. In: Fahn et al. (eds) Recent Developments in Parkinson's Disease. Vol. II. Macmillan Healthcare Information, Florham Park, N.J., pp. 153-163, 293-304). However, the UPDRS score only records the effect of an active substance on the symptoms of Parkinson's disease. It does not allow any statements to be made with regard to whether or not an active substance has an influence on the destruction of dopaminergic cells, which is the underlying cause of the symptoms.

Metman et al. (2001) *Clin. Neuropharmacol.* 24:163 also describe the effect of rotigotine on motor disturbances associated with Parkinson's disease. The treated patients already had pronounced dyskinesias, which were improved by administering rotigotine.

Thus, substituted 2-aminotetralins, in particular rotigotine, are known from the prior art as a dopamine agonist for the symptomatic treatment of Parkinson's disease. However, Parkinson medicaments that only have an effect on the symptoms do not promise any advantage with regard to the preventive treatment of Parkinson's disease since they do not have any influence on the destruction of dopaminergic cells or on the progression and/or onset of the disease.

Experimental tests have now surprisingly shown that the substituted 2-aminotetralins of the general formula I

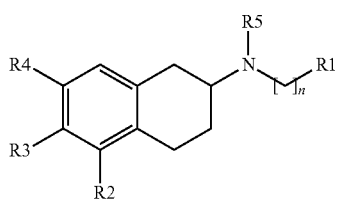

wherein
n is 1 to 5;
R2 is OA; R3 and R4 are each independently selected from H and OA; with A being selected from H, alkyl, alkoxymethyl or a group

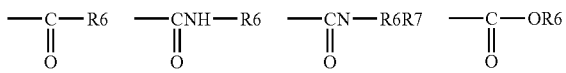

wherein R6 and R7 are each independently alkyl, in particular C1-20 alkyl and particularly preferred C1-6 alkyl, or aryl, in particular optionally substituted phenyl;
R5 is a C1-3 alkyl;
R1 is a group selected from hydrogen, 3-pyridyl, 4-pyridyl, optionally substituted phenyl,

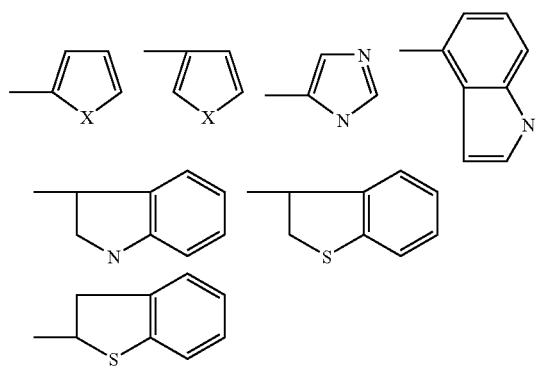

wherein X is selected from S, O or NH;
wherein the compound of formula I can be present as a racemate or as a pure (R)- or (S)-enantiomer, as well as physiologically acceptable salts of these compounds, which had hitherto only been used for the symptomatic therapy of Parkinson's disease, have neuroprotective properties and they can thus be used as a medicament and/or prophylactic agent for the prevention of dopaminergic cell loss in particular in very early stages of Parkinson's disease or in high-risk patients.

FIGURES

FIG. 1 shows representative examples of the neuroprotective effect of rotigotine measured on the basis of the density of the dopamine transporters as an indication of the density of the remaining nerve endings in the striatum. Groups 1 to 7 were treated as follows: Group 1: untreated control group; Group 2: control group treated with a vehicle solution for rotigotine and MPTP; Group 3: MPTP treatment; Group 4: MPTP treatment plus rotigotine 0.3 mg/kg; Group 5: MPTP treatment plus rotigotine 1.0 mg/kg; Group 6: MPTP treatment plus rotigotine 3.0 mg/kg; Group 7: treatment solely with rotigotine (3.0 mg/kg).

FIG. 2 shows dopamine transporter (DAT) binding in the dorsal and ventral part of the striatum in different groups by quantifying the DAT density according to an experiment as shown in FIG. 1. Bar graphs 1 to 7 correspond to groups 1 to 7 as shown in FIG. 1. The groups marked with * displayed a significant decline in DAT binding as compared to the control group 2. The groups marked with # displayed a significant gain in DAT binding as compared to the MPTP-treated Group 3.

DESCRIPTION OF THE INVENTION

Apoptotic processes are supposed to play an important role in the destruction of dopaminergic neurones in the pathogenesis of Parkinson's disease (Barzilai (2001) *Cell Mol. Neurobiol.* 21:215). Neuroprotective substances that can stop or even reverse dopaminergic cell destruction are thus desired. The MPTP model is thereby deemed to be predictive of the required neuroprotective characteristics (Dawson (2002) *Nature Neuroscience Supplement* 5:1058).

Rotigotine surprisingly shows the desired pharmacological profile in both an acute and a sub-acute MPTP model. The test results suggest that apoptotic processes are prevented by rotigotine.

The 2-aminotetralins according to the invention, in particular rotigotine, thereby display a neuroprotective effect in a mouse model of Parkinson's disease: Following the acute administration of MPTP, which causes Parkinson's syndrome in both humans and monkeys, the number of the degenerating neurones in the acute phase was measured on the one hand (Table 1) and the functional integrity of the striatum in the sub-acute phase was ascertained on the other by determining the density of the dopamine transporter in the terminal nerve endings (FIGS. 1 and 2). It could be demonstrated in both cases that rotigotine had a neuroprotective effect: On the one hand, the number of degenerating neurones in the mesencephalon was reduced following the administration of rotigotine and on the other hand, the dopaminergic innervation of the striatum was almost completely maintained or restored.

TABLE 1

Number of degenerating neurones in the mouse, shown by FluoroJade staining

| Group | No. of degenerating neurones | Standard deviation |
|---|---|---|
| 1: Vehicle-treated control group | 2.0 | 2.4 |
| 2: MPTP intoxication | 73.5 | 34.0 |
| 3: MPTP intoxication + rotigotine 0.3 mg/kg | 66.7 | 30.5 |
| 4: MPTP intoxication + rotigotine 1.0 mg/kg | 76.8 | 41.6 |
| 5: MPTP intoxication + rotigotine 3.0 mg/kg | 34.9 | 31.9 |
| 5: MPTP - vehicle + rotigotine 3.0 mg/kg | 3.8 | 4.3 |

In a pilot study, the neuroprotective effect of rotigotine on monkeys was also examined.

In the model used, which reflects the progressive course of morbus Parkinson in primates, monkeys (macaques) were injected with subliminal toxic doses of MPTP for several days. Parkinson's symptoms developed in the model over a period of approximately 2 weeks. As soon as a certain level of damage had been reached, rotigotine was injected daily in a formulation that produced a continuous plasma level over 24 hours. The MPTP injections were stopped as soon as the motor activity had been reduced to a certain extent (approximately 5 days later). The behavior of the animals was assessed on a daily basis. Six weeks after the start of MPTP administration, the rotigotine injections were stopped and the animals were observed for a further two weeks without treatment. It was observed that the motor activity of the animals clearly improved during treatment and also in the following clearance phase.

A group of animals was killed at the end of both the rotigotine administration and the clearance phase, and the condition of the basal ganglia was histologically and biochemically examined. The density of the nerve endings in the striatum had significantly increased as compared to the untreated animals. The content of pre-pro-enkephalin, which is an indicator of the intact network in the "indirect pathway" of the basal ganglia, showed a tendency towards normalisation following treatment and the clearance phase.

The results show that the neuroprotective potential of rotigotine can also be proven in a primate model of morbus Parkinson. A neuroprotective effect can therefore also be expected in humans.

Thus, with rotigotine and structurally related substituted 2-aminotetralins of the general formula I, active substances were provided for therapy, which are ideally suitable for producing medicaments and/or prophylactic agents for the prevention of dopaminergic neurone loss.

A subject matter of the present application is therefore the use of substituted 2-aminotetralins of the general formula I, which is given below, as well as, in particular, rotigotine for the production of a medicament for the treatment or prevention of dopaminergic neurone loss in patients suffering from a neurodegenerative disease that is associated with increased dopaminergic cell destruction or in patients having an increased risk of augmented dopaminergic cell destruction.

Increased dopaminergic neurone loss regularly occurs in patients with Parkinson's disease, however, it is also frequently observed in other neurodegenerative diseases, for example, in alpha-synucleopathies or in Huntington's disease as well as in REM sleep disturbances and olfactory disorders.

As compared to the hitherto use of the aminotetralins of formula I, in particular rotigotine, which was limited solely to the symptomatic treatment of Parkinson's patients with motor disturbances, the prophylactic treatment of individuals displaying less than two of the cardinal symptoms of Parkinson's disease and who thus require neuroprotective, prophylactic therapy rather than symptomatic therapy, has been developed as a new area of use. As already described above, such individuals profit in particular from the neuroprotective effect of rotigotine since owing to the administration of rotigotine, dopaminergic cell loss is stopped or slowed down at a time when a higher number of dopaminergic neurones are still present than is the case in patients already displaying motor symptoms.

A subject matter of the invention is therefore the use of substituted 2-aminotetralins of the general formula I

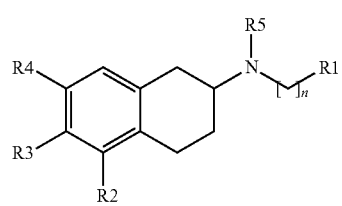

wherein n is 1 to 5;

R2 is OA; R3 and R4 are each independently selected from H and OA; with A being selected from H, alkyl, alkoxymethyl or a group

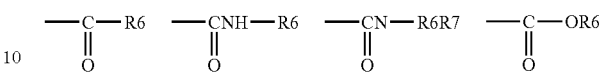

wherein R6 and R7 are each independently alkyl, in particular C1-20 alkyl and particularly preferred C1-6 alkyl, or aryl, in particular optionally substituted phenyl;

R5 is a C1-3 alkyl;

R1 is a group selected from hydrogen, 3-pyridyl, 4-pyridyl, optionally substituted phenyl,

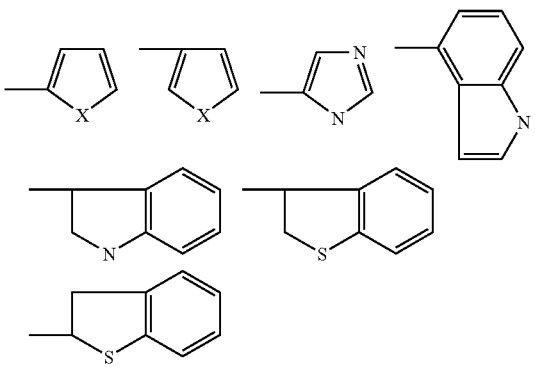

wherein X is selected from S, O or NH;

wherein the compound of formula I can be present as a racemate or as a pure (R)- or (S)-enantiomer, as well as physiologically acceptable salts of these compounds, for the preventive treatment of Parkinson's disease, in particular for the prevention of dopaminergic cell loss in individuals in whom, before commencement of the preventive treatment, at least three of the four cardinal symptoms of the group bradykinesia, rigidity, resting tremors and postural instability are not yet present or are only rudimentary or partially present.

Compounds that are particularly suitable for the production of a neuroprotective agent or a prophylactic agent for Parkinson's disease are those in which R2 is an OA group and R3 and R4 are independently H or an OA group, it being particularly preferred for A to be a hydrogen atom or a group

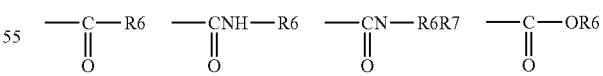

in which R6 is a C1-20 alkyl, in particular C1-12 alkyl or C1-6 alkyl, phenyl or methoxyphenyl.

In another preferred embodiment of the invention R4 is H.

In another preferred embodiment of the invention R3 is H.

In another preferred embodiment of the invention R3 and R4 are both H.

In another preferred embodiment of the invention n=1, 2 or 3, in particular n=2 or 3.

R1 is preferably selected from the group H,

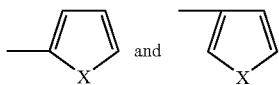

wherein X is selected from S, O and NH and wherein it is especially preferred for X to be a sulphur atom.

It is especially preferred for R1 to be 2-thienyl.

In a further preferred embodiment of the invention, R5 is a C3-alkyl, in particular n-propyl.

In a further preferred embodiment of the invention, R1 is a 2-thienyl, R3 and

R4 are both H, R5 is a C3 alkyl and n=2.

In a particularly preferred embodiment of the invention, the racemate of (+/−) 5,6,7,8-tetrahydro-6-[propyl[2-(2-thienyl)ethyl]amino]-1-naphthol, and especially preferred the pure S-enantiomer of this compound (rotigotine), is used for the production of the prophylactic agent for Parkinson's disease.

The terms "C1-20 alkyl", "C1-12 alkyl" and "C1-3 alkyl" are each to be understood as branched or non-branched alkyl groups with the corresponding number of C-atoms. For example, a "C1-20 alkyl" includes all alkyls with 1 to 20 C-atoms. The alkyls can be optionally substituted, e.g. with halogen. The alkyls are preferably present in non-substituted form.

The term "alkoxymethyl" is to be understood as the group —CH2-O-alkyl. A preferred alkyl is a C1-12 alkyl, a C1-6 alkyl or a C1-3 alkyl.

The individuals to be prophylactically treated with the substituted 2-aminotetralins can be apparently healthy individuals, whose genetic or epidemic predisposition may not indicate an increased risk of developing Parkinson's disease.

In particular high-risk individuals or patients in whom early clinical, clinical/chemical or clinical/physical symptoms can be detected, but who, however, do not yet display two or more of the cardinal symptoms of Parkinson's disease, come into consideration for treatment with substituted 2-aminotetralins, in particular, rotigotine.

Finally, 2-aminotetralins, in particular rotigotine, can also be used as a neuroprotective agent if the diagnosis is not clear, but development of the symptoms towards Parkinson-like neurodegeneration can be expected.

Prevention of neuronal cell loss is required in particular by (a) individuals with an increased risk of Parkinson's disease, or (b) individuals with early symptoms of Parkinson's disease.

The terms "morbus Parkinson" and "Parkinson's disease" are used as synonyms in this patent application and include idiopathic and genetic Parkinson's disease. The so-called Parkinson-Plus syndrome as well as secondary Parkinsonism are to be differentiated therefrom.

The term "cardinal symptoms" of Parkinson's disease is to be understood in this patent application as one or more of the symptoms of bradykinesia, rigidity, resting tremors and postural instability.

"Individuals with an increased risk of Parkinson's disease" are to be understood in this patent application in particular as individuals who do not yet display any detectable symptoms of Parkinson's disease, but who have certain risk factors.

Such risk factors can be genetic mutations (Nussbaum (2003) *N. Engl. J. Med.* 348:25). For example, the parkin gene on chromosome 6q25.2-27 (PARK2) is associated with juvenile Parkinsonism and occurs more frequently in families with autosomal recessive Parkinson inheritance (Matsumine (1997) *Am. J. Hum. Genet.* 60:588; Kitada (1998) *Nature* 392:605; Abbas (1999) *Hum. Mol. Genet.* 8:567; Tassin (1998) *Am. J. Hum. Genet.* 63:88; Lucking (2000) *N. Engl. J. Med.* 342:1560-1567). Other gene loci, for example, PARK6 and PARK7, were also found with increased frequency in families with juvenile, recessively-inherited Parkinson's disease (Valente (2001) *Am. J. Hum. Genet.* 68:895; van Dujin (2001) *Am. J. Hum. Genet.* 69:629). Mutations in the alpha-synuclein gene (PARK1) were detected in families with juvenile, autosomal dominantly-inherited Parkinson's disease (Polymeropoulos (1997) *Science* 276:2045). In addition to genetic predisposition, environmental influences, such as high exposure to, for example, insecticides (Vanacore (2002) *Neurol Sci.* 23 (Suppl. 2): 119) can also represent risk factors.

In this patent application, "individuals with early symptoms of Parkinson's disease" are to be understood in particular as individuals in whom at least three of the four cardinal symptoms (rigidity, resting tremors, bradykinesia and postural instability) are not yet present, or are only rudimentarily or partially present, but who manifest diagnostically useable early clinical, clinical/biochemical and/or clinical/physical symptoms.

Clinical/biochemical markers can be modifications in the alpha synuclein or neuromelanin pattern. Such modifications can be due, for instance, to the expression of genetic variants, for example of alpha synuclein, the development of aggregates or filaments, for example of alpha synuclein, or the increased release from cellular stores, for example, from the cytoplasms of cells that are being destroyed, as is the case with neuromelanin.

Early clinical/physical symptoms can be structural or functional changes to the brain, which can be physically detected, for example, by means of PET and SPECT studies, by means of transcranial sonography (Becker (2002) *J. Neurol.* 249 (Suppl. 3:III):40; Prunier et al. (2003) Neuroimage 19(3): 810-816) or by detecting biochemical markers such as neuromelanin (WO 02/31499).

Early clinical symptoms can be olfactory disorders, depression, impairments of visual and cognitive functions or sleep disorders, whereby a combination of different tests can also be used for early diagnosis (Becker (2002) *J. Neurol.* 249(Suppl. 3:III):40; Stem (2004) *Ann. Neurol.* 56:169).

As already discussed above, approximately 70% to 80% of the dopaminergic neurones of the substantia nigra have already been destroyed by the time at least two of the four cardinal symptoms have manifested themselves for the first time. In order to effectively use the surprising neuroprotective potential of the aminotetralins of formula I, in particular of rotigotine, the prophylactic treatment of the patients is therefore preferably initiated at a stage when the patients have a lower loss of dopaminergic cells of the substantia nigra (SN). Individuals displaying just one or none of the cardinal symptoms of Parkinson's disease in a clearly pronounced form are therefore preferably treated.

Individuals displaying a dopaminergic cell loss in the SN of less than 70%, 60%, 50% and particular preferred of less than 40%, 30%, 20% or 10% are preferably treated.

Two scores can be used as aids for diagnosing and controlling the therapy of patients already displaying noticeable motor disturbances, i.e. the UPDRS score and the Hoehn and Yahr score.

In a preferred aspect of the invention, the group of patients prophylactically treated with the aminotetralins of formula I, in particular with rotigotine, furthermore has a modified Hoehn and Yahr score of 0 to 2, particularly preferred of 0 to 1 and especially preferred of 0.

TABLE 2

Modified stage determination according to Hoehn
(1992) Neurologic Clinics 10:331

| | |
|---|---|
| Stage 0 | No sign of disease |
| Stage 1 | Unilateral disease |
| Stage 1.5 | Unilateral plus axial involvement |
| Stage 2 | Bilateral disease without impairment of balance |
| Stage 2.5 | Mild bilateral disease with recovery on pull test |
| Stage 3 | Mild to moderate bilateral disease: slight postural instability; physically independent |
| Stage 4 | Severe disability; still able to walk or stand unaided |
| Stage 5 | Wheelchair-bound or bedridden unless aided |

Patients with a UPDRS score, part III (see embodiment 5), of at least 10 are normally classified as patients who can be considered for dopaminergic therapy. However, the group of patients suitable for benefiting from the neuroprotective effect of substituted 2-aminotetralins of formula I, in particular rotigotine, preferably has a very low or undetectable motor UPDRS score (part III). Within the meaning of the present invention, the preventive treatment with substituted 2-aminotetralins of formula I, in particular with rotigotine, should therefore preferably be carried out on patients having a UPDRS motor score of less than 10, 9, 8, 7, 6, 5, 4, 3, 2 or 1. It is particularly preferred for the patients to still not display any motor disturbances at all.

The terms "prevention", "prophylaxis" and "preventive treatment" are used as synonyms in this patent application. They include, in particular, the administration of a medicament to individuals in whom at least three of the four cardinal symptoms of Parkinson's disease (rigidity, resting tremors, bradykinesia, postural instability), are not yet present, or are only rudimentarily or partially present, in order to prevent or delay the appearance or significant development of the motor symptoms of Parkinson's disease and/or further dopaminergic neurone loss, particularly in the substantia nigra. The individuals to be prophylactically treated preferably do not yet display any of the cardinal symptoms in a distinctly pronounced form.

Compounds of formula I are optically active and can be present as racemates or as pure (R)- or (S)-enantiomers. In this patent application, the term "pure enantiomer" is understood to mean that a substance is preferably present to at least 90 mol % in the form of one enantiomer, e.g. in the (S) form, whilst the proportion of the respective other enantiomer, e.g. the (R) form, is correspondingly low. If, for example, rotigotine ((−)-5,6,7,8-tetrahydro-6-[propyl[2-(2-thienyl)ethyl] amino]-1-naphthol) is used to produce the medicament according to the invention, the (R)-(+)-enantiomer is preferably present in a proportion of <10 mol %, particularly preferred in a proportion of <2 mol % and especially preferred in a mole proportion of <1%, based on the total amount of rotigotine in the prophylactic agent for Parkinson's disease.

Compounds of formula I can be present in the medicament as free bases or in the form of the physiologically acceptable salts, e.g. in the form of rotigotine hydrochloride.

"Physiologically acceptable salts" include non-toxic addition salts of a compound of formula (I) in the form of the free base, with organic or inorganic acids. Examples of inorganic acids include HCl.

There are many methods of application available for administering substituted 2-aminotetralins of formula I, in particular rotigotine, which the person skilled in the art can select and adapt depending on the need, condition and age of the patient, the required dosage and the desired application interval.

A preferred mode of administering substituted 2-aminotetralins of formula I, in particular rotigotine, is transdermal administration. The form of administration may, in principle, be selected from, for example, an ointment, a paste, a spray, a film, a plaster or an iontophoretic device.

Substituted 2-aminotetralins of formula I, in particular rotigotine, are preferably applied to the skin of the patient in plaster form, with the active substance preferably being present in a matrix of adhesive polymer, for instance a self-adhesive polysiloxane. Examples of suitable transdermal formulations can be found in WO 99/49852, WO 02/89777 and WO 02/89778. Such a form of administration enables a substantially constant plasma level to be established and therefore a constant dopaminergic stimulation over the entire application interval (WO 02/89778; Metman (2001) Clin. Neuropharmacol. 24:163).

If, on the other hand, a medicament in the form of a subcutaneous or intramuscular depot form is desired, substituted 2-aminotetralins of formula I, in particular rotigotine, may be suspended, for example as salt crystals, for instance as crystalline rotigotine hydrochloride, in a hydrophobic anhydrous medium and injected, such as described in WO 02/15903, or else administered in the form of microcapsules, microparticles or implants based on biodegradable polymers, such as described, for example, in WO 02/38646.

Other conceivable forms of administering substituted 2-aminotetralins of formula I, in particular rotigotine, are transmucosal formulations, for example sublingual sprays, rectal formulations or aerosols for pulmonary administration.

Suitable dosages of substituted 2-aminotetralins of formula I, in particular rotigotine, are between 0.05 and approximately 50 mg/day, with daily doses of preferably between 0.1 and 40 mg and in particular of between 0.2 and 20 mg/day being administered. Dosage can thereby take place in a gradually increasing manner, i.e. the treatment may optionally start with low doses which are then increased until the maintenance dose is reached.

It is clear to the person skilled in the art that the dosage interval may vary depending on the applied quantity, the mode of application and the daily requirement of the patient. Thus, a transdermal form of application may be designed, for example, for administration once a day, once every three days or once every seven days, whilst a subcutaneous or intramuscular depot can make it possible to administer injections, for example, in one-weekly, two-weekly or four-weekly cycles.

Other active substances which prevent the progression of dopaminergic cell loss can also be present in the neuroprotective medicament in addition to the substituted 2-aminotetralins of formula I, in particular in addition to rotigotine.

Examples hereof are substances with an anti-apoptotic effect (minocycline, FK-506, cyclosporine A, zVAD) as well as neurotrophins such as, for example, Glial-cell-derived neurotrophic factor (GDNF).

In a combination preparation, a sequential administration can be achieved, for example, in that an administration form, for example an oral tablet, has two different layers with differing release profiles for the different pharmaceutically active ingredients. It is clear to the person skilled in the art that various forms of administration and application patterns are conceivable within the context of the present invention, which all form subject matter of the invention.

A further subject matter of the application is a kit for the early diagnosis and treatment of morbus Parkinson. Such a kit contains (a) a diagnostic agent that enables the diagnosis of Parkinson's disease and/or the predisposition to develop Parkinson's disease at an early or asymptomatic stage as well as
(b) a pharmaceutical formulation containing substituted 2-aminotetralins of general formula I, in particular rotigotine.

Such a kit may comprise, for example:
(a) an agent or a diagnosis kit for detecting neuromelanin,
(b) a pharmaceutical formulation containing substituted 2-aminotetralins of general formula I, in particular rotigotine.

In another embodiment of the invention, the kit may contain:
(a) an agent or a diagnosis kit for detecting semaphorin 3,
(b) a pharmaceutical formulation containing substituted 2-aminotetralins of general formula I, in particular rotigotine.

In another embodiment of the invention, the kit may contain:
(c) an agent or a diagnosis kit for detecting alpha-synuclein and/or its aggregates,
(d) a pharmaceutical formulation containing substituted 2-aminotetralins of general formula I, in particular rotigotine.

In a further embodiment of the invention, the kit may contain:
(a) an agent or a diagnosis kit for genetically detecting a mutation associated with the appearance of Parkinson's disease and/or an allele associated with the more frequent appearance of Parkinson's disease, in particular, from the group of PARK genes 1, 2, 3, 4, 5, 6, 7 or 8 as well as the gene loci CYP2D6-B and GSTM1,
(b) a pharmaceutical formulation containing substituted 2-aminotetralins of general formula I, in particular rotigotine.

EMBODIMENTS

Embodiment 1

Rotigotine Plaster 1.8 g of rotigotine (free base) were dissolved in 2.4 g of ethanol and added to 0.4 g of Kollidon 90F (dissolved in 1 g of ethanol). This mixture was added to a 74% solution of silicone polymers (8.9 g of BioPSA 7-4201+8.9 g of BIO-PSA 7-4301 [Dow Corning]) in heptane. Following the addition of 2.65 g of petrol ether, the mixture was stirred for 1 hour at 700 rpm in order to obtain a homogeneous dispersion. Following lamination on polyester, it was dried at 50° C. The final weight of the plaster was 50 g/cm2.

Embodiment 2

Rotigotine Depot Suspensions (a) 1411.2 g of Miglyol 812 were weighed into a Duran flask. 14.4 g of Imwitor 312 were added to the Miglyol and then heated for 30 minutes to 80° C. whilst being stirred. The clear solution was cooled to room temperature and filtered.

(b) 1188 g of the solution produced in (a) were transferred into a glass laboratory reactor, 12 g of N-0923 were added and homogenised for 10 minutes under nitrogen with an Ultraturrax at 10,000 rpm. The suspension was decanted into brown glass bottles whilst the Ultraturrax was running (2,000 rpm).

Embodiment 3

Sub-Acute MPTP Model

For the purpose of intoxication, 80 mg/kg of the neurotoxin 1-methyl-4-phenyl-1,2,3,6-tetrahydro-pyridine (MPTP) were administered to mice (in doses of 20 mg/kg at two-hour intervals, groups 3 to 6 in FIGS. 1 and 2), which led to the degeneration of approximately 50 to 60% of the neurones of the substantia nigra (maximum degeneration in group 3 in FIGS. 1 and 2). Rotigotine was administered daily for 7 days in doses of 0.3, 1 or 3 mg/kg respectively as the so-called "slow-release formulation" (see embodiment 2) (groups 4 to 6 in FIGS. 1 and 2). A group of MPTP-treated animals (group 3) was given a rotigotine vehicle solution (see embodiment 2 without rotigotine HCl) and served as a reference. Groups 1, 2 and 7 served as controls, whereby group 1 did not receive any treatment at all, group 2 was treated with the vehicle solutions for MPTP and rotigotine and group 7 received exclusively rotigotine. The animals were killed on day 8 and their brains were removed and frozen. The frozen sections were incubated with 100 pm [$^{125}$I] PE2I ([$^{125}$I]-(E)-N(3-iodoprop-2-enyl)-2β-carboxymethyl-3β-(4'-methylphenyl)-nortropane) in phosphate buffer, pH 7.4, in order to mark the amount of dopamine transporters still present in the striatum, which indicates the number of functioning nerve endings. Rotigotine improved the survival of the neurones and their nerve endings depending on the dosage. This is a clear indication of the neuroprotective properties of the substance (FIGS. 1 and 2).

Embodiment 4

Acute MPTP Model (Including Apoptosis)

For the purpose of intoxication, 80 mg/kg of the neurotoxin 1-methyl-4-phenyl-1,2,3,6-tetrahydro-pyridine (MPTP) were administered to mice (in doses of 20 mg/kg at two-hour intervals), which led to the degeneration of approximately 50 to 60% of the neurones of the substantia nigra. Approximately 16 hours beforehand, rotigotine was administered in doses of 0.3, 1 or 3 mg/kg respectively, as the so-called "slow-release formulation". Diffusion and absorption latencies led to rotigotine then being optimally available when MPTP was administered. The animals were killed after 24 hours and their brains fixed. The brain sections were stained with FluoroJade to identify degenerating cells. The immunohistochemical marking of tyrosine-hydroxylase helped to identify dopaminergic neurones. The staining of tyrosine hydroxylase did not display any differences between the treated and untreated animals; staining with FluoroJade showed a large number of degenerating neurones; the neurones had, however, not yet been completely removed; this suggests that the cell destruction occurs apoptotically. The number of degenerating neurones was approximately 50% less following application of rotigotine, which further demonstrates the neuroprotective property of the substance (Table 1).

Embodiment 5

Determination of the Motor UPDRS Score

The motor UPDRS score (part III of the UPDRS score) is determined by examining the patient using criteria 18 to 31 as given below in Table 2, with the point scores resulting for each of the criterion being respectively added together.

TABLE 2

III. MOTOR EXAMINATION
18. Speech:
- ☐ 0 - Normal.
- ☐ 1 - Slight loss of expression, diction and/or volume.
- ☐ 2 - Monotone, slurred but understandable; moderately impaired.
- ☐ 3 - Marked impairment, difficult to understand.
- ☐ 4 - Unintelligible.

19. Facial Expression:
- ☐ 0 - Normal.
- ☐ 1 - Minimal hypomimia, could be a normal "poker face".
- ☐ 2 - Slight but definitely abnormal diminution of facial expression.
- ☐ 3 - Moderate hypomimia; lips parted some of the time.
- ☐ 4 - Masked or fixed face with severe or complete loss of expression; lips parted by 7 mm.

20. Tremor at rest: (F = face, RH = right hand, LH = left hand, RF = right foot, LF = left foot)

| F | RH | LH | RF | LF | |
|---|----|----|----|----|----|
| ☐ | ☐ | ☐ | ☐ | ☐ | 0 - Absent. |
| ☐ | ☐ | ☐ | ☐ | ☐ | 1 - Slight and infrequently present. |
| ☐ | ☐ | ☐ | ☐ | ☐ | 2 - Mild in amplitude and persistent; or moderate in amplitude but only intermittently present. |
| ☐ | ☐ | ☐ | ☐ | ☐ | 3 - Moderate in amplitude and present most of the time. |
| ☐ | ☐ | ☐ | ☐ | ☐ | 4 - Marked in amplitude and present most of the time. |

21. Action or Postural Tremor of the Hands: (R = right, L = left)

| R | L | |
|---|---|----|
| ☐ | ☐ | 0 - Absent. |
| ☐ | ☐ | 1 - Slight; present with action. |
| ☐ | ☐ | 2 - Moderate in amplitude, present with action. |
| ☐ | ☐ | 3 - Moderate in amplitude, present with posture holding as well as action. |
| ☐ | ☐ | 4 - Marked in amplitude; interferes with eating. |

22. Rigidity: (Judged on passive movement of major joints on a patient in the sitting position. Cogwheeling can be ignored). (N = neck, RUE = right upper extremity, LUE = left upper extremity, RLE = right lower extremity, LLE = left lower extremity).

| N | RUE | LUE | RLE | LLE | |
|---|-----|-----|-----|-----|----|
| ☐ | ☐ | ☐ | ☐ | ☐ | 0 - Absent. |
| ☐ | ☐ | ☐ | ☐ | ☐ | 1 - Slight or detectable only when activated by mirror-image or other movements. |
| ☐ | ☐ | ☐ | ☐ | ☐ | 2 - Mild to moderate. |
| ☐ | ☐ | ☐ | ☐ | ☐ | 3 - Marked, but full range of motion still achievable. |
| ☐ | ☐ | ☐ | ☐ | ☐ | 4 - Severe, difficulty in carrying out all movements. |

23. Finger Taps: (Patient taps thumb against index finger in rapid succession with maximum possible amplitude and separately with each hand). (R = right, L = left).

| R | L | |
|---|---|----|
| ☐ | ☐ | 0 - Normal. |
| ☐ | ☐ | 1 - Slight slowing and/or reduction in amplitude. |
| ☐ | ☐ | 2 - Moderately restricted. Distinct and premature fatiguing. Movement may occasionally be interrupted. |
| ☐ | ☐ | 3 - Severely restricted. Delayed start of the movements or interruption of continuous movements. |
| ☐ | ☐ | 4 - Can barely perform the task. |

24. Hand Movements: (Patient opens and closes the hands in rapid succession with greatest possible amplitude and separately with each hand). (R = right, L = left).

| R | L | |
|---|---|----|
| ☐ | ☐ | 0 - Normal. |
| ☐ | ☐ | 1 - Slight slowing and/or reduction in amplitude. |
| ☐ | ☐ | 2 - Moderately restricted. Distinct and premature fatiguing. Movement may occasionally be interrupted. |
| ☐ | ☐ | 3 - Severely restricted. Delayed start of the movements or interruption of continuous movements. |
| ☐ | ☐ | 4 - Can barely perform the task. |

25. Rapid Alternating Movements of the Hands: (pronation/supination movements of the hands, vertically or horizontally, with largest possible amplitude, both hands simultaneously).

| R | L | |
|---|---|----|
| ☐ | ☐ | 0 - Normal. |
| ☐ | ☐ | 1 - Slight slowing and/or reduction in amplitude. |
| ☐ | ☐ | 2 - Moderately restricted. Distinct and premature fatiguing. Movement may occasionally be interrupted. |
| ☐ | ☐ | 3 - Severely restricted. Delayed start of the movements or interruption of continuous movements. |
| ☐ | ☐ | 4 - Can barely perform the task. |

26. Leg Agility: (Patient taps heel on the ground in rapid succession thereby lifting the entire leg. Amplitude should be at least 7.5 cm).

| R | L | |
|---|---|----|
| ☐ | ☐ | 0 - Normal. |
| ☐ | ☐ | 1 - Slight slowing and/or reduction in amplitude. |
| ☐ | ☐ | 2 - Moderately restricted. Distinct and premature fatiguing. Movement may occasionally be interrupted. |

TABLE 2-continued

☐ ☐ 3 - Severely restricted. Delayed start of the movements or interruption of continuous movements.
☐ ☐ 4 - Can barely perform the task.

27. Rising from Chair: (Patient attempts to rise from a straight-back wooden or metal chair with arms folded across chest).
  ☐ 0 - Normal.
  ☐ 1 - Slow; may need more than one attempt.
  ☐ 2 - Pushes self up using arms of seat.
  ☐ 3 - Tends to fall back and may possibly have to make several attempts, but can rise without assistance.
  ☐ 4 - Unable to rise without assistance.

28. Posture:
  ☐ 0 - Normal erect.
  ☐ 1 - Not quite erect, slightly stooped posture; could be normal for an older person.
  ☐ 2 - Moderately stooped posture, definitely abnormal; can be leaning slightly to one side.
  ☐ 3 - Severely stooped posture with kyphosis; can be leaning moderately to one side.
  ☐ 4 - Marked flexion with extremely abnormal posture.

29. Gait:
  ☐ 0 - Normal.
  ☐ 1 - Walks slowly, may shuffle a few short steps, but no festination or propulsion.
  ☐ 2 - Walks with difficulty, but requires little or no assistance; possibly slight festination, short steps or propulsion.
  ☐ 3 - Severe disturbance of gait, requires assistance.
  ☐ 4 - Cannot walk at all, even with assistance.

30. Postural Stability: (Response to sudden rearwards displacement caused by pulling on the patient's shoulders whilst patient is erect and has their eyes open and feet slightly apart. Patient is prepared.)
  ☐ 0 - Normal.
  ☐ 1 - Retropulsion, but recovers unaided.
  ☐ 2 - No postural response; would fall if not caught by examiner.
  ☐ 3 - Very unstable, tends to lose balance spontaneously.
  ☐ 4 - Unable to stand without assistance.

31. Body Bradykinesia and Hypokinesia: (Combination of slowness, hesitancy, decreased arm-swing, small movement amplitude and poverty of movement in general.)
  ☐ 0 - None.
  ☐ 1 - Minimal slowing, movement is intentional; could be normal for some persons. Possibly reduced amplitude.
  ☐ 2 - Slight slowing and poverty of movement, which is clearly abnormal. Alternatively also reduced amplitude.
  ☐ 3 - Moderate slowing and poverty of movement or reduction in amplitude.
  ☐ 4 - Marked slowing, poverty of movement or reduction in amplitude.

Embodiment 6

In Vitro Conversion of a Prodrug into the Active Substance

The microsome fraction that contains the essential metabolising enzymes is obtained from the liver cell homogenates of a human, monkey, dog, rat or mouse by means of differential centrifugation; the cytoplasmatic fraction can alternatively also be obtained. The subcellular fraction is suspended with a buffer such that a solution having a defined protein content is obtained. Following the addition of 1 µM of the prodrug to be tested, incubation takes place at 37° C. for 60 min. Rotigotine is then quantified by means of HPLC/UV or also by means of HPLC/MS and is related to the used amount. The concentration or time series are examined for detailed analyses.

The invention claimed is:

1. A method for treatment of dopaminergic cell loss in a subject or decreasing the progression of Parkinson's disease in a subject, comprising
   (a) identifying a subject without clinically confirmed Parkinson's disease; and
   (b) administering to the subject rotigotine or a physiologically acceptable salt thereof.

2. The method of claim 1, wherein the subject has at least one clinical symptom selected from the group consisting of an olfactory disorder, depression, a sleep disorder of the "REM behavior disorder" type, constipation and a short-term movement anomaly.

3. The method of claim 1, wherein the subject displays a mutation in a PARK gene and/or a modification to alpha synuclein or neuromelanin pattern.

4. The method of claim 1, wherein the subject displays a dopaminergic cell loss in substantia nigra of less than 60% before administering rotigotine.

5. The method of claim 1, wherein the subject has a UPDRS motor score of less than 10 before administering rotigotine.

6. The method of claim 1, wherein the subject has a Hoehn-Yahr score of 0 or 1.

7. The method of claim 1, wherein rotigotine is administered parenterally, transdermally or mucosally.

8. The method of claim 1, wherein rotigotine is administered in a dose of 0.05 to 50 mg per day.

9. The method of claim 1, wherein the subject has one, two or three symptoms selected from the group consisting of rigor, resting tremor, bradykinesia and postural instability, to a partial degree.

10. A method for treatment of dopaminergic cell loss in a subject or decreasing the progression of Parkinson's disease in a subject, comprising
   (a) identifying a subject without any of four cardinal symptoms of Parkinson's disease but having an increased risk of developing Parkinson's disease; and (b) administering to the subject rotigotine or a physiologically acceptable salt thereof.

11. The method of claim 10, wherein the subject displays a mutation in a PARK gene and/or a modification to alpha synuclein or neuromelanin pattern.

12. The method of claim 1, wherein the subject displays a dopaminergic cell loss in substantia nigra of less than 50% before administering rotigotine.

* * * * *